(12) United States Patent
Garito et al.

(10) Patent No.: US 7,947,037 B1
(45) Date of Patent: May 24, 2011

(54) COSMETIC RF SURGERY

(75) Inventors: Jon C. Garito, Oceanside, NY (US);
Alan G. Ellman, Oceanside, NY (US)

(73) Assignee: Ellman International, Inc., Oceanside, NY (US)

( * ) Notice: Subject to any disclaimer, the term of this patent is extended or adjusted under 35 U.S.C. 154(b) by 1126 days.

(21) Appl. No.: 11/655,720

(22) Filed: Jan. 22, 2007

(51) Int. Cl.
*A61B 18/14* (2006.01)
(52) U.S. Cl. .................. 606/32; 606/41; 606/49
(58) Field of Classification Search .............. 606/41, 606/49, 32
See application file for complete search history.

(56) References Cited

U.S. PATENT DOCUMENTS

| 5,733,282 | A  | * | 3/1998 | Ellman et al. | 606/45 |
| 6,228,078 | B1 | * | 5/2001 | Eggers et al. | 606/32 |
| 6,572,613 | B1 | * | 6/2003 | Ellman et al. | 606/45 |
| 2002/0077626 | A1 | * | 6/2002 | Ellman et al. | 606/41 |
| 2003/0153906 | A1 | * | 8/2003 | Sharkey et al. | 606/41 |

* cited by examiner

*Primary Examiner* — Lee S Cohen

(57) ABSTRACT

An electrode and procedure for removing skin lesions or blemishes comprising an electrode with a flat blunt active end which is applied to the skin lesion or blemish, while RF electrosurgical currents are applied to the electrode, in an up and down tapping motion in such manner that contact between the skin and the active electrode end is intermittent. Preferably, after a small number of skin taps with the electrode end, the tapped area is wiped with a wet gauze or cloth, and the procedure of intermittent tapping with the RF electrode interrupted with wet wipes is continued until the blemish disappears.

6 Claims, 1 Drawing Sheet

COSMETIC RF SURGERY

This invention relates to a procedure for cosmetically treating skin tissue using non-ablative radio-frequency (RF) energy. It also relates to a monopolar electrode for use in such procedures.

BACKGROUND OF THE INVENTION

With the emerging trend of aesthetic medical therapy, several modalities have been developed to further the drive for human self-preservation. Cosmetic and oculoplastic surgery have increasingly crossed paths in the pursuit of noninvasive procedures with which to rejuvenate human skin, mostly facial skin. One of the recent innovations in oculofacial surgery involves the use of nonablative laser and light sources to reduce the appearance of facial creases. However, disadvantages of laser-based treatments include the necessity for multiple treatments and results that may regress or have unpredictable results. Moreover, the efficacy of such systems done on cases with severe skin laxity does not appear satisfactory in some patients.

Recent advances in management of flaccid skin disorders have led to the development of radiofrequency treatments. Several devices have been developed to deliver radiofrequency energy in a non-ablative fashion that generates heat through resistance in the dermis and subcutaneous tissue to improve facial rhytides and skin laxity.

A typical method of using electrosurgery to remove facial lesions was to shave them with loop shaped electrodes. The surgeon needed to use a great deal of skill to avoid creating a deep divot into the skin below the lesion borders. Putting pressure on the handpiece holding the loop electrode tended to produce a divot that was very difficult to heal and often created scarring, delayed healing and excess pain as a result of going too deep into the tissue. A major disadvantage as a result was that the learning curve to master the cosmetic procedure of removing facial and all skin blemishes with a loop electrode was long.

Other typical methods of removing superficial lesions are scalpels, curettes, electrosurgery devices, cryosurgery methods, and lasers. Scalpels cut or incise out the lesion. Curettes scrape out the lesion in divots. Electrosurgery burns the lesion out. Cryosurgery freezes in depth. Lasers burn the lesion out. While the aim in superficial lesion removal, especially in the facial areas, should be to do so with the least amount of consequent tissue destruction, excessive tissue trauma (necrosis of tissues) will tend to result in increased fibrosis with any of the above surgical tools. The greater the penetration into the skin from the trauma-causing-modality, the more likely it is that scarring will result. Scarring is unacceptable when it occurs after treatment of very superficial skin lesions of a cosmetic nature.

SUMMARY OF THE INVENTION

An object of the present invention is to employ radio-frequency energy for removing skin, especially facial, lesions with non-ablative electrodes to reduce skin conditions that impair the beauty of natural healthy skin and avoid many of the disadvantages of the prior art.

In accordance with a feature of the invention, a monopolar electrode is used that is specially configured to provide a small-area, reasonably uniform electric field distribution at the skin surface being treated. Preferably, the active end of the electrode is flat and blunt.

In accordance with a further feature of the invention, the flat blunt active electrode end is applied to the skin lesion or blemish, while RF electrosurgical currents are applied to the electrode, in an up and down tapping motion in such manner that contact between the skin and the active electrode end is intermittent. Preferably, after a small number of skin taps with the electrode end, the tapped area is wiped with a wet gauze or cloth, and the procedure of intermittent tapping with the RF electrode interrupted with wet wipes is continued until the blemish disappears. While applicants do not wish to be limited to the following explanation, it is believed that the flat blunt end spreads the RF energy over a small area, as distinguished from concentrating the energy with a pointed electrode, and the distribution of the energy combined with the intermittent application of the electrode end tends to prevent over-heating of the surrounding skin tissue and thus the RF ablative effect is focused on the blemished tissue to be removed. It is also believed that the intermittent wiping with wet gauze also contributes to preventing over-heating of the skin tissue.

Preferably, the electrode tip is also bio-compatible and of a highly conductive material, which also contributes to low skin temperatures. Silver and gold alloys are preferred for the composition of the electrode end.

It is also preferred that not only is the power setting of the radio-frequency-generating instrument set low, but also the cuticoag mode is selected. In the cuticoag mode, the radio-frequency waveform at a preferred frequency in the 3.8-4 MHz range is fully rectified before being supplied to the electrode.

In a preferred embodiment, the highly conductive electrode material is an alloy comprised mainly of silver with a small percentage of ingredients added to strengthen the silver alloy electrode and preserve its luster.

It is believed that radiofrequency technology produces an electric current that generates heat through resistance in the dermis and subcutaneous tissue. The thermal effect depends on the conductivity features of the treated tissue. Non-ablative RF treatment has a lower risk of complications, shorter recovery time and less disruption of regular activities.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similar elements.

BRIEF DESCRIPTION OF THE DRAWINGS

In the drawings:

FIG. 3 is a partly cross-sectional, partly side view of another form of monopolar electrode according to the invention.

DETAILED DESCRIPTION OF PREFERRED EMBODIMENTS

Figure 1:
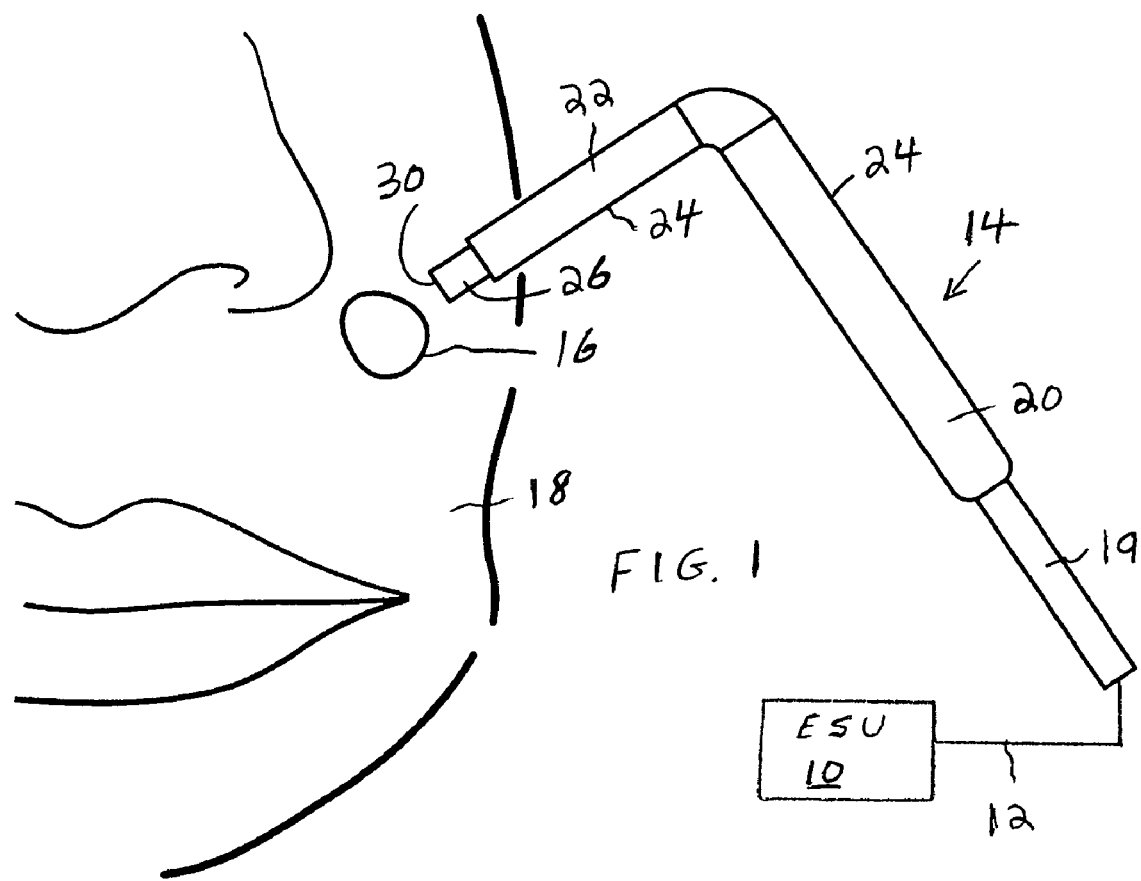
FIG. 1 is a schematic view of one form of a monopolar electrode according to the invention shown being applied to a face mole of a patient.
Figure 2:
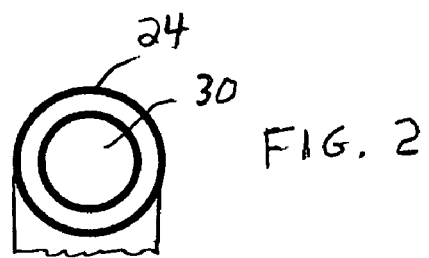
FIG. 2 is an end view of the active end of the electrode of FIG. 1.

In the present application, FIG. 1 is a schematic view of one form of radio-frequency generating instrument 10 connected 12 to a conventional handpiece (not shown) in which is mounted a monopolar electrode 14 in accordance with the invention. For simplicity, the instrument 10 is labeled ESU as an abbreviation for an electrosurgical unit. The electrode 14 is shown being applied to a mole 16 on the face 18 of a patient. The handpiece may have a conventional front end adapted to receive and hold rigidly the conductive shank end 19 of the electrode 14 comprising a proximate axial portion 20 and a distal portion 22 which is bent at an angle of about 90° to the axial portion 20. Except for the shank end 19 in the handpiece which is uncoated, most of the remaining part of the electrode is coated with an insulating coating 24. The most distal end portion 26, which is also uncoated, constitutes the working end whose end surface 30, an end view of which is shown in FIG. 2, is flat and blunt. The handpiece is electrically-insulating or if conductive is covered with an electrically-insulating coating. The electrode 14 is long enough to be applied by a surgeon as shown such that the bare flat surface 30 over its whole circular area can contact any blemished surface region 16 of exposed skin of the patient, typically the facial site where most skin treatments are desired.

While the uncoated portion of the entire electrode 14 is preferably made of solid metal, it is also possible that only the working end 26 is made of a highly conductive metal such as silver or gold welded or brazed to the conductive metal. The remainder of the electrode can be made of the usual metals such as brass or tungsten or stainless steel. If desired, small additions of other metals, such as germanium or indium can be added to the silver or gold to harden the electrode or reduce tarnishing. The working end should preferably also be biocompatible. The high conductivity property assists in producing low tissue temperatures on the skin and also minimizes sticking.

The preferred electrode should have a range of diameters from about 0.009 to 0.095 inches. The electrode is flattened on its tip and preferably has a right angle in its configuration.

The RF electrode in accordance with the invention together with the method of using the electrode by applying it on its flattened tip side to the skin blemish offers many important advantages to the cosmetic surgeon and aesthetician.

As one example of a suitable procedure, the operator would simply draw a border around the cosmetic blemish or lesion with a skin marking pen. Then a local anesthetic injection would be introduced for larger lesions. For smaller lesions topical anesthetics such as emla-cream or cryo-sprays could be used for numbing purposes.

The radiosurgical unit 10 is placed preferably in a mode in which the waveforms produced comprise continuously rectified currents and the RF electrode brought to the skin lesion 16. The operator with the handpiece and electrode 14 over the skin lesion energizes the electrode by stepping on the usual foot peddle or using the handpiece fingerswitch buttons.

The operator then gently begins to simply tap the lesion 16 with the flat tip 30 over the lesion surface just to the skin borders. After a series of tapping motions it will be observed that the action has ablated loose tissue fragments from the lesion and these can then be wiped away with a moist gauze. This procedure is repeated over the total lesion until it is substantially completely removed.

The results will be highly pleasing to both patient and operator. The margin of error of going too deeply is completely removed. There is a great deal of safety built into this electrode design and method of removing unsightly skin lesions and blemishes.

In some cases the physician may want to perform a biopsy of the skin lesion prior to its removal. In this case a loop electrode may be used to skim the top of the skin lesion off to send to a pathologist. The remainder of the skin lesion would then be removed with the tapping RF electrode of the invention in the same manner as described above.

A big advantage of electrode of the invention is that it now becomes a safe, effective, and efficient non-ablative skin-blemish-removal procedure that can be utilized by cosmeticians as well as surgeons. The reason that cosmeticians can now use this method is that the non-ablative action involved does not go below the skin level and thus the user does not require surgical training.

In the previous description, the intermittent tapping action was generated entirely by the operator. An up and down motion can be assisted by incorporating a spring inside the electrode which will reduce some of the effort required by the operator. This embodiment is illustrated in FIG. 3. The spring 34 is indicated schematically inside the electrode tip, whose working end still possesses the flat blunt surface 30.

Another way not shown of obtaining the intermittent tapping action is by incorporating a mechanism similar to that of an electric toothbrush, which uses a small toy motor to rotate a spindle to which the brush end is connected. By interposing a non-symmetrical cam between the rotating spindle end and the electrode tip as is well known, the rotating action is converted into a reciprocating or up and down motion.

In this description, by "axial" is meant parallel to the long axis of the electrode (in line with the shank 19 in FIG. 1). By "lateral" is meant transverse to the long axis of the electrode. "Lateral" is intended to include 90°+/−about 5°

Other usable mechanical or electrical structures following the teachings of the prior patent will be appreciated by those skilled in this art. As with the embodiments of the prior application, the insulating coating 24 will prevent accidental touching of patient tissue by the electrode sides, so that the discharge is localized to the region underneath the bare end 30. The surgeon positions the electrode 326 so as to touch or press lightly on the tissue to be treated as needed for the procedure being followed.

As explained below, the preferred metal for the working end of the electrode is a highly electrically-conductive and thermally conductive material, a silver alloy being preferred. For cost reasons, the silver alloy shank can be supported in a tube of a suitable electrically-conductive metal such as brass or stainless steel, brass being preferred because it has a higher thermal conductivity. A suitable thickness of the insulator 34 is about 0.02-0.04 inches. The diameter of the working end can vary between about 1/16 and 3/32 inches. Preferably, the overall length of the angled electrode from tip 30 to the opposite shank end is about 1.5-3 inches, the length of the right angled end being about 1/3-5/8 inches.

The radio-frequency apparatus 10 preferably used outputs high frequency (RF) radio-frequency currents in the range of about 3.8-4.0 MHz. The use of 3.8-4.0 MHz radio-frequency currents at low powers with a monopolar electrode with a flat blunt end applied intermittently maintains the surface below a harmful temperature to avoid burning. The use of a highly thermally-conductive silver alloy also helps. The preferred silver alloy electrode is solid metal constituted mainly of silver with a small amount of germanium and indium to increase its hardness and resistance to corrosion. The compositions described in our copending application Ser. No. 11/180,809, filed Jul. 14, 2006, the contents of which are herein incorporated by reference, are deemed suitable for this application with the solid electrode rather than the laminated coated electrode being preferred. In general, the silver alloy preferably has a content by weight of about 93-98% by weight silver with about 1.5-4% by weight of germanium and 1-2% by weight of indium. A preferred composition is 97% silver with 2% germanium and 1% indium.

Examples of suitable radio-frequency generating apparatus are the Model SURGITRON Dual-Frequency and IEC radio-frequency units manufactured by and available from Ellman International, Inc. of Oceanside, N.Y. .

The major advantages of the RF electrode and procedure of the invention, coupled with the RF energy, include that there is no pressure applied to the lesion. A gentle tapping of the lesion vaporizes and liquefies the lesion without burning surrounding healthy skin and without the trauma caused by penetrating the skin tissue, and the effects are limited to the superficial dermis. The flat blunt end of the electrode ensures no penetration of the skin. Another significant advantage is that local hair follicles are left intact and not destroyed. There tends to be no scarring, no discoloration of surrounding healthy tissue or skin, no erythema, no swelling, and no pain. Another advantage is that these superficial lesions can be removed with topical anesthesia eliminating local injectable anesthetics. Examples of topical anesthetic creams are Ela-Max and EMLA.

In summary, radiofrequency skin lesion removal is a new and very promising tool for non-surgical cosmetic treatments. This procedure is believed to be an effective, non-invasive, economical and safe tool. In addition, costs connected to this new method are rather low, and even less skilled professionals can be easily trained on this technology, thanks to the low risks that its use involves.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A procedure for improving the appearance of skin tissue of a patient by removing lesions, comprising the steps:
   A. providing:
      (a) a handpiece and an electrode comprising an elongated first member having a proximal first end mounted in the handpiece and a distal second end being the active end of the electrode,
      (b) the second end being approximately at right angles to the first end and being bare and configured to form a flat blunt end;
   B. providing a radio-frequency generating instrument for supplying radio-frequency currents in the megacycle range to the electrode when activated;
   C. applying the flat blunt end of the electrode to the patient's skin tissue to be treated and continuously moving the electrode up and down in and out of contact with the skin surface such that radio-frequency currents are intermittently applied to the patient's skin by the electrode's active end while the radio-frequency instrument is activated to remove surface layers of the lesion being treated.

2. A procedure as claimed in claim 1, further comprising the step of:
   D. when surface layers of the lesion being treated have separated following step C, wiping off the separated tissue with a wet gauze;
   E. repeating steps C. and D. until the lesion is substantially completely removed.

3. A procedure as claimed in claim 2, wherein the bare active end of the electrode is constituted of an alloy primarily of silver.

4. A procedure as claimed in claim 3, wherein the alloy is primarily of silver with small additions of germanium and indium.

5. A procedure as claimed in claim 1, wherein the radio-frequency currents are at a frequency of about 3.8-4 MHz.

6. A procedure as claimed in claim 5, wherein the radio-frequency currents are continuously rectified.

* * * * *